United States Patent [19]
Gray

[11] Patent Number: 6,019,745
[45] Date of Patent: Feb. 1, 2000

[54] SYRINGES AND SYRINGE PUMPS

[75] Inventor: John Martyn Gray, Wetherby, United Kingdom

[73] Assignee: Zeneca Limited, London, United Kingdom

[21] Appl. No.: 09/207,668

[22] Filed: Dec. 9, 1998

Related U.S. Application Data

[62] Division of application No. 08/545,706, Nov. 3, 1995, Pat. No. 5,882,338.

[51] Int. Cl.[7] .......................................... A61M 1/00
[52] U.S. Cl. ............................................. 604/131; 604/152
[58] Field of Search ................................... 604/131, 151, 604/153, 154, 152; 340/571, 572

[56] References Cited

U.S. PATENT DOCUMENTS

| | | | |
|---|---|---|---|
| 3,809,871 | 5/1974 | Howard et al. | 604/131 X |
| 4,270,532 | 6/1981 | Franetzki et al. | 604/151 |
| 4,282,872 | 8/1981 | Franetzki et al. | 604/131 X |
| 4,469,481 | 9/1984 | Kobayashi | 604/131 X |
| 4,510,489 | 4/1985 | Anderson, III et al. | 340/572 |
| 4,510,490 | 4/1985 | Anderson, III et al. | 340/572 |
| 4,560,979 | 12/1985 | Rosskopf | 604/131 X |
| 4,741,736 | 5/1988 | Brown | 604/131 X |
| 4,886,495 | 12/1989 | Reynolds | 604/88 |
| 5,242,408 | 9/1993 | Jhuboo | 604/152 |
| 5,254,096 | 10/1993 | Rondelet et al. | 604/152 |
| 5,383,858 | 1/1995 | Reilly et al. | 604/131 X |
| 5,429,401 | 7/1995 | Leslie et al. | 604/131 |

FOREIGN PATENT DOCUMENTS

| | | |
|---|---|---|
| 2266641 | 12/1975 | France . |
| 2555744 | 5/1985 | France . |
| 40 20522 | 1/1992 | Germany . |
| 9308204.5 | 9/1993 | Germany . |
| 155687 | 4/1991 | Japan . |
| 89/08264 | 9/1989 | WIPO . |
| 91 00307 | 1/1991 | WIPO . |
| 91 04759 | 4/1991 | WIPO . |
| 92 12402 | 7/1992 | WIPO . |
| 93 02720 | 2/1993 | WIPO . |
| 94/12235 | 6/1994 | WIPO . |

OTHER PUBLICATIONS

Graseby 3100 Syringe Pump, Graseby Medical Ltd., A Cambridge Electronic Industries Companiy, England, 2 pages, 1993.

50 Ways to Touch Memory, Second Edition, Dallas Semiconductor, Dallas, Texas, Oct. 1992, pp. 1–26.

*Primary Examiner*—Max Hindenburg
*Attorney, Agent, or Firm*—Pillsbury Madison & Sutro, LLP Intellectual Property Group

[57] ABSTRACT

A medical syringe comprises a cylindrical barrel 1 having therein a plunger 4 which can be axially driven by a plunger rod 3. The plunger rod 3 passes through an aperture in the centre of a finger grip 2 having two finger grip projections 2b at opposite sides thereof. A data carrier means in the form of an electrically or magnetically operable device 2c is mounted near the end of one of the two finger grip projections 2b, with preferably a device 2c mounted near the end of each finger grip projection 2b. The device 2c carries data relating to the medicament contained or to be contained within the syringe, and can be read by a suitably adapted syringe pump when the syringe is mounted thereon to be driven by the syringe pump.

9 Claims, 5 Drawing Sheets

SYRINGES AND SYRINGE PUMPS

This is a division of application Ser. No. 08/545,706, filed Nov. 3, 1995, now U.S. Pat. No. 5,882,338.

This invention relates to syringes and syringe pumps and more particularly, but not necessarily exclusively, to such devices applied to the delivery of medicament, including anaesthetics, to medical patients.

Syringes have been in use for many years for delivering medicament, including anaesthetics, by doctors and nurses to medical patients, both inside and outside hospitals. Originally, syringes were always operated manually by the doctor or nurse. Manual operation of a syringe is not however suitable where the medicament is to be delivered to the patient at an accurately controlled rate over a relatively long period of time.

A more recent development is that of the syringe pump, being a device upon which a syringe containing medicament can be mounted. The syringe is securely retained on the syringe pump, and the plunger rod of the syringe is engaged by a drive device which can move in the axial direction of the mounted syringe in order to deliver medicament therefrom. In some types of syringe pump the drive device is a linearly-acting member constrained to move in a straight line along the syringe pump, whereas in other types of syringe pump the drive device can comprise a rotary screw cooperable with a fixed nut. When the screw is driven in rotation it cooperates with the fixed nut and moves axially to drive the syringe plunger rod.

Conventionally, the syringe is filled with medicament by the doctor or nurse and properly located on the syringe pump. The syringe pump comprises computer control means for controlling the syringe drive device and comprising a keyboard and display. The doctor or nurse can program the computer control means through the keyboard, setting for example the continuous medicament flow rate which is required for the particular patient concerned, and the duration of the infusion which is required.

There is disclosed in International Publication No. WO 91/04759 a syringe pump which can operate with a syringe having a bar code thereon to program the computer control means with data for a particular patient's dosage requirements. Instead of these data being inputted via a keyboard the pharmacist prepares the programming bar code and applies it to the syringe, when he has filled the syringe, in dependence upon a prescription tailored to the patient's requirements and provided by the patient's physician. The patient mounts the bar coded syringe on the syringe pump, which programs the computer control means automatically via a bar code reader.

The syringe pump is thereby driven entirely in accordance with the physician's prescription, which prevents injury to the patient through his or her improper operation of the syringe pump keyboard. It is possible for the patient to modify the dispensing of the medicament to some extent, for example if a supplemental dose is required, but the physician's data applied to the syringe by means of a bar code by the pharmacist would limit the amounts and frequency of taking the medicament so as to prevent the patient injuring him or herself.

Hereinbefore it has been assumed that the syringe is always filled with medicament by the doctor, nurse or, in the latter example, by the pharmacist. There has however been a proposal for drug manufacturers to supply syringes, pre-filled with their products, for example to hospitals. It would then simply remain for the appropriate hospital personnel to place the pre-filled syringe on a syringe pump, which would then drive the syringe plunger rod at a controllable rate and for a controllable time, which could be entered via the keyboard by the doctor or nurse in accordance with the patient's requirements. There thus need be no transfer of medicament from a vial or bottle to the syringe, and moreover there is no intervention by physician or pharmacist in providing the medicament-filled syringe or the instructions for its use.

It is an object of the present invention to provide with a syringe, which preferably but not essentially is pre-filled as described hereinbefore, a data carrier means to carry data relating to a medicament contained, or to be contained, in the syringe, which data carrier means can be read by a suitably adapted syringe pump to take into account the data carried. The data carrier means may be present with the syringe when it is sold by the manufacturer of the medicament and/or the syringe to a hospital or pharmacist for example, which is particularly advantageous when the syringe is a pre-filled syringe.

According to a first aspect of the present invention there is provided a syringe having data carrier means therewith to carry data relating to a medicament contained or to be contained in the syringe, wherein the data carrier means comprises an electrically and/or magnetically operable device to emit data it is carrying in response to activation by a suitable field applied by an external means.

The syringe may be of a conventional design employing for example a cylindrical barrel and a plunger, although it is to be appreciated that the invention is equally applicable to alternative designs of syringe.

Thus, any container for medicament which is subjected to positive pressure in use, thereby to deliver the medicament, can qualify as a syringe for the purposes of the present invention.

An example of such an alternative design of syringe could comprise a flexible container, for example a flexible bag or bulb, which is pressurised in use by a cooperable pump to drive medicament from the bag or bulb when contained therein.

According to a second aspect of the present invention there is provided a syringe pump cooperable with a syringe according to the first aspect of the present invention, and comprising activation means to emit a field suitable to cause the electrically and/or magnetically operable device with the syringe to emit data it is carrying, the syringe pump further comprising receiving means for receiving the data thus emitted, drive means for operating the syringe to deliver to a patient medicament when contained in the syringe, and control means coupled to said receiving means and to said drive means to operate the latter taking into account data received from the data carrier means by the receiving means.

According to a third aspect of the present invention there is provided a syringe according to the first aspect of the present invention when operably combined with a syringe pump according to the second aspect of the present invention.

According to a fourth aspect of the present invention there is provided a method for automatically identifying a medicament or a property of a medicament, comprising providing with a syringe which contains or is to contain the medicament, data carrier means comprising an electrically and/or magnetically operable device to emit data it is carrying, and identifying said medicament or said property thereof, in response to activation by a suitable field applied by an external means.

According to a fifth aspect of the present invention there is provided a partially disassembled syringe comprising a barrel, a plunger and a finger grip in an assembled state with the plunger fitting closely within the barrel and the finger grip being inserted in an open end of the barrel, there being a plunger rod provided separately for subsequent assembly with the plunger, and the syringe being provided with data carrier means to carry data relating to a medicament contained or to be contained in the syringe, wherein the data carrier means comprises an electrically and/or magnetically operable device to emit data it is carrying in response to activation by a suitable field applied by an external means.

Syringes according to the first or fifth aspect of the present invention may be manufactured and sold, preferably pre-filled, in large numbers to hospitals and pharmacists. There need be no application to the syringes of dosage data and the like, which can be programmed into the syringe pump at the point of use depending upon the particular patient's requirements.

When a syringe as described is mounted on a cooperable syringe pump, the medicament-related data may be transferred automatically or on request to the control means of the syringe pump. This data may comprise an identification of the medicament contained within the syringe, and/or its concentration. Other medicament-related data could be employed alternatively or in addition, for example batch number and expiry date.

Since the syringe-mounted data need not be entered to the syringe pump via a keyboard for example, the responsibilities of the syringe pump operator can be reduced as regards the information to be inputted, and the data carrier means can operate as a recognition device to ensure that the correct syringe is mounted on the syringe pump for the particular application concerned. This eliminates incorrect, and possibly dangerous, administration as a result of operator error.

Various types of device can be used as the data carrier means in embodiments of the present invention. Preferred embodiments may employ electrically and/or magnetically resonant systems, for example a magnetostrictive system wherein the data carrier device comprises one or more strips of magnetically biased material, which will mechanically resonate when activated by an external source of a magnetic field. The resonance will be detected by the receiving means of the syringe pump, the value of the resonant frequency detected supplying an item of data.

Alternatively, an electronic transponder could be used which outputs data bits when activated by a field in the form of an interrogating power burst via one or more antennae in the syringe pump.

As far as the magnetostrictive embodiments are concerned, single magnetic strips may provide respective discrete bits of information corresponding to their individual fundamental resonant frequencies, or a single magnetic strip can be magnetised to respond to its fundamental resonant frequency and also, or alternatively, to harmonics of that fundamental resonant frequency.

Preferably a data carrying device is mounted on or in a projection or other part of the syringe, for example on one side of a finger grip thereof. When the syringe is mounted on a cooperable syringe pump, the projection may project into a groove or recess on the syringe pump to cooperate with an activation means and receiving means within the body of the syringe pump, preferably in the vicinity of the groove or recess.

An advantage with the activatable proposed embodiments of the present invention may be that contact and/or relative movement need not be taking place between the data carrier and the receiving means for the data to be read, leading to good reading reliability. Moreover the optical cleanliness required with a prior art bar code reader, for example of the window through which the scanner sees the bar code, is not a problem. Extraneous matter could in principle however interfere with efficient operation of a bar code reader. Moreover, in the optical system the bar code would have to be accurately positioned rotationally to align with the reader. Finally, an optical bar code system may be capable of being misused, and may not provide the required safety.

Preferred embodiments of the present invention require no contact or relative movement during reading, leading to reliability, simplicity and convenience in operation.

For a better understanding of the present invention and to show how it may be put into effect, reference will now be made, by way of example, to the accompanying drawings in which.

Figure 1:
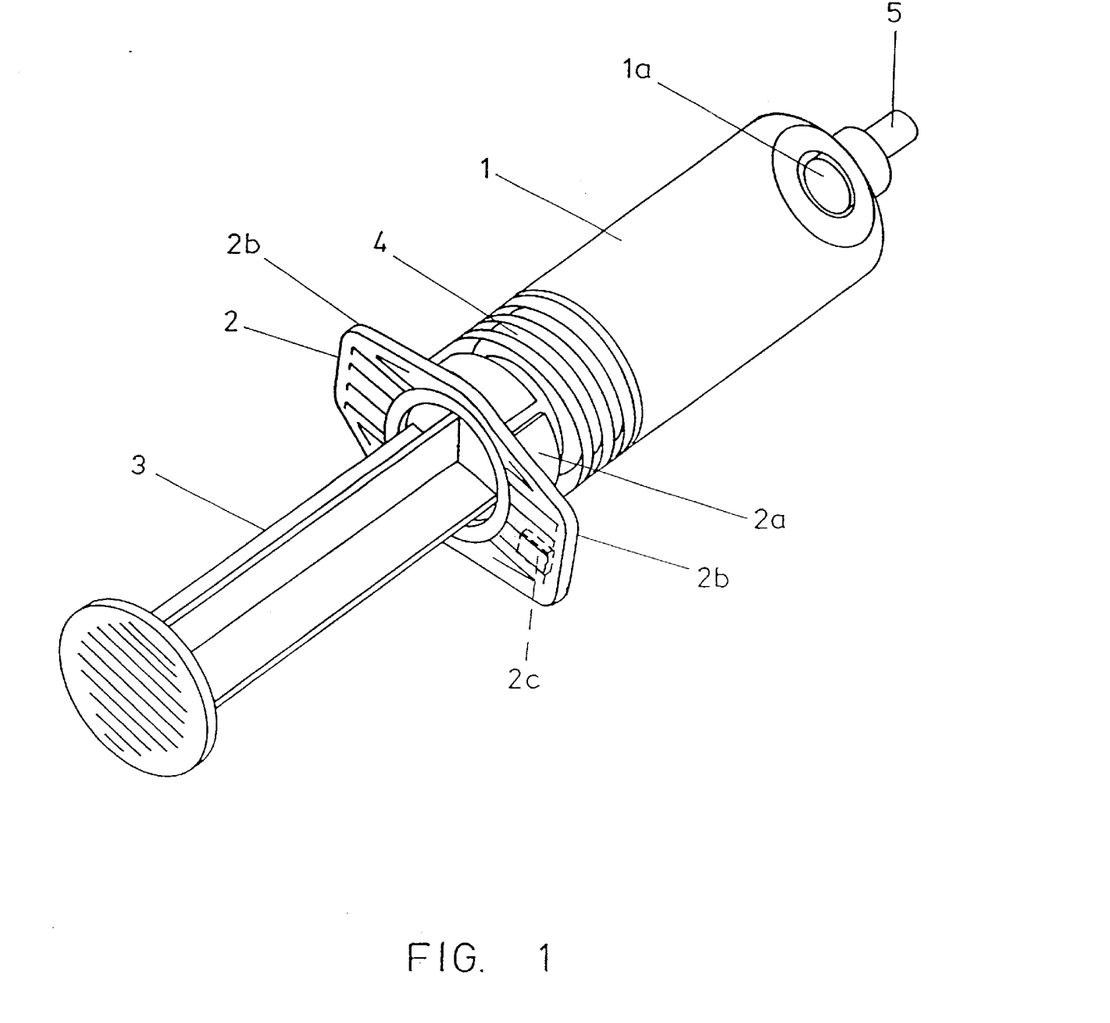
FIG. 1 shows an assembled pre-filled syringe according to the first aspect of the present invention.

FIG. 1 shows an assembled pre-filled medical syringe comprising a cylindrical glass barrel 1 having an open left-hand end wherein is inserted a split annular portion 2a of a plastics finger grip 2, locating lateral projections 2b of the finger grip 2 on the end of the glass barrel 1 such that the projections 2b extend in opposite directions laterally away from the axis of the cylindrical glass barrel 1.

In manual use of the syringe, the glass barrel 1 will be held between the first two fingers of the operator's hand, with the two lateral projections 2b of the finger grip 2 preventing the syringe from sliding between those two fingers.

A data carrier means in the form of an electrically (including electronically) or magnetically operable device 2c is mounted near the end of one of the two finger grip projections 2b, and details of this device 2c will be provided hereinafter. Preferably however a device 2c is mounted near the end of each finger grip projection 2b, to provide operability irrespective of the rotational alignment of the syringe.

A syringe plunger rod 3 is attached at its forward end to a rubber plunger 4 fitting closely within the glass barrel 1, and a Luer connector 5 is attached to the front end of the glass barrel 1, a rubber stopper 1a sealing that forward end.

The syringe is pre-filled with medicament between the rubber plunger 4 and the forward end of the glass barrel 1.

Upon delivery to the hospital from the manufacturer of the medicament, the pre-filled syringe is disassembled to some extent and pre-packaged. The glass barrel 1, the rubber plunger 4, and the finger grip 2 are packed in a preassembled state, with the rubber stopper 1a being inserted at the front end of the glass barrel 1 to retain the medicament. The plunger rod 3 is packaged alongside the glass barrel 1 in order to save axial space in the package.

When it is required to use the packaged pre-filled syringe, the glass barrel 1 and the plunger rod 3 are removed from the package and assembled together, with the rod 3 being screwed into a thread on plunger 4, and the connector 5 is then fitted by the medical staff. A needle (not shown) in the connector 5 pierces the rubber stopper 1a.

When packaged, the pre-filled syringe is provided with various other protective components which are not relevant to the present invention and which are not shown or discussed in detail here.

The particular pre-filled syringe which has been shown and described is the pre-filled syringe being developed, without the data carrier means 2c, for the administration of the intravenous anaesthetic 'DIPRIVAN'.

Figure 2:
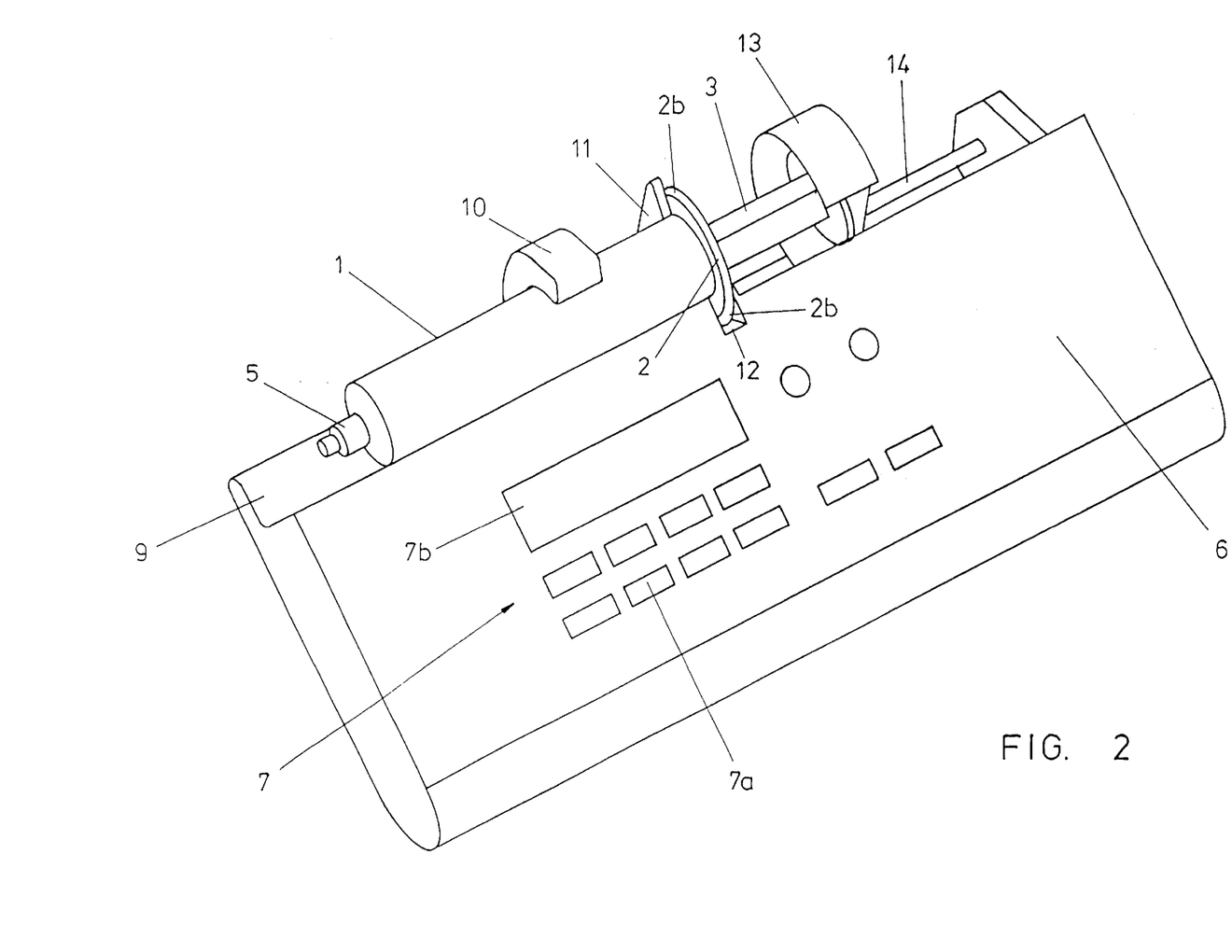
FIG. 2 shows the syringe of FIG. 1 when mounted on a cooperable syringe pump according to the second aspect of the present invention, thereby to provide a combination according to the third aspect of the present invention.

FIG. 2 shows the assembled pre-filled syringe of FIG. 1 when mounted on a syringe pump 6 and with the syringe partly emptied.

The syringe pump 6 comprises control means 7 including a microprocessor within the body of the syringe pump 6 and an associated keyboard 7a and display 7b. Various other switches and also alarm indicators are provided on the body of the syringe pump 6, which will be apparent to the man skilled in the art and which are not shown here in detail.

The syringe pump 6 comprises at its upper edge a longitudinal trough 9 into which the glass barrel 1 of the syringe fits. For simplicity the contents of the glass barrel 1 are not shown in FIG. 2. A pivotable clamp 10 and a stop 11 together secure the syringe on the syringe pump 6 within the trough 9. The clamp 10 prevents mainly lateral movement of the syringe, whilst the stop 11 abuts against an upper one of the projections 2b of the finger grip 2 to prevent axial movement of the syringe in the forward direction.

The lower lateral projection 2b of the finger grip 2 is provided with the data carrier device 2c (not visible in FIG. 2) and projects lower than the trough 9 into a locating groove or recess 12 therein.

A syringe drive means of the syringe pump 6 comprises a linearly operating hooded piston 13 which slides along a smooth locating rod 14 extending parallel to the axis of the syringe. The piston 13 is actuated by a drive motor from within the body of the syringe pump 6, as will be apparent to the man skilled in the art.

When the syringe is mounted on the syringe pump 6 as shown in FIG. 2, the data carrier device 2c is located within the body of the syringe pump 6 by means of recess 12. There, it is activated by a suitable field generating activation means within the interior of the body of the syringe pump 6, adjacent the recess 12 and external of the syringe itself. The data carrier device 2c thereby emits the data it is carrying as will be described in more detail hereinafter. Also as described hereinafter in more detail, receiving means within the interior of the body of the syringe pump 6 and adjacent the recess 12 receive the data thus emitted.

The drive means, including piston 13, for operating the syringe to deliver medicament contained therein to a patient, is operated by the control means 7 taking into account the data received from the syringe by the receiving means and fed to the control means 7. If that data relates to the medicament in the syringe only, the control means 7 will need to be programmed fully by an operator using the keyboard 7a and display 7b, as regards for example delivery rate and delivery duration, or target blood concentration where appropriate.

Thus, it is envisaged that the emitted data will contain at least an identification of the drug contained in the syringe and/or its concentration, although this could be extended to include further data such as for example the batch number of the medicament and its expiry date. Alternative data could be employed also.

The particular syringe pump which has been shown and described is the 3100 syringe pump conventionally manufactured and sold by Graseby Medical Ltd of Watford, UK without the activation means and the receiving means. It is to be understood that activation and receiving means can also be incorporated into other designs and makes of syringe pump.

Although the present invention has been particularly described and illustrated thus far with reference to a pre-filled syringe, it is to be appreciated that the syringe need not be pre-filled for example by the manufacturer, but could be filled for example within a hospital. Thus, the present invention is intended also to cover embodiments of the syringe wherein there is no medicament in the syringe initially, but wherein it is intended to fill the syringe with a particular medicament identified by the data carrier device which is mounted on the syringe during its manufacture or possibly later.

Turning now to the details of the data carrier device 2c, the possibility has already been mentioned of employing a transponder with a suitable activation means and receiving means. Such systems are available in a variety of packages for other applications and are commercially available from, for example, the company Texas Instruments and are known under the title Texas Instruments Registration and Identification Systems (TIRIS).

Figure 3:
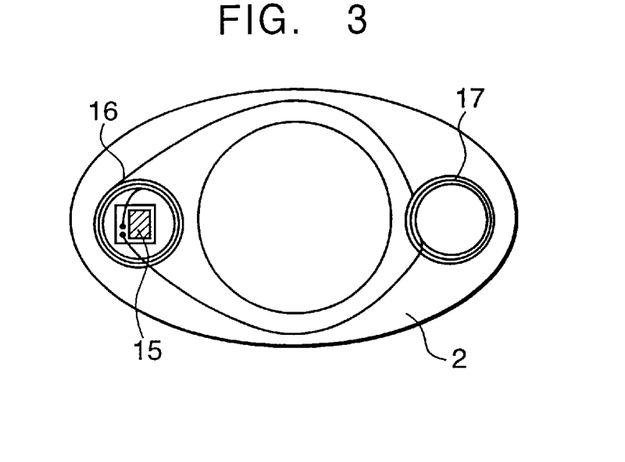
FIG. 3 shows, an embodiment of syringe finger grip.

FIG. 3 shows how a transponder 15 mounted on a chip carrier may be connected to two contrawound aerial coils 16,17 and encapsulated within the syringe finger grip 2. Upon receipt of power at an appropriate frequency by one or both of the aerial coils 16, 17, the transponder 15 will emit its pre-programmed data from the same aerial coil or coils.

The system would alternatively operate with a single aerial coil wound around the axis of the syringe, however the implementation described above is preferable, as the aerial coils 16,17 are positioned such that when the syringe is mounted on the pump 6, a coil enters the groove 12 in the pump case where the activation means' sending/receiving coil is mounted—reducing the power requirement of the transmitter. In addition, the balanced nature of the aerial minimises the risk of crosstalk between other pumps and syringes similarly equipped.

Figure 4:
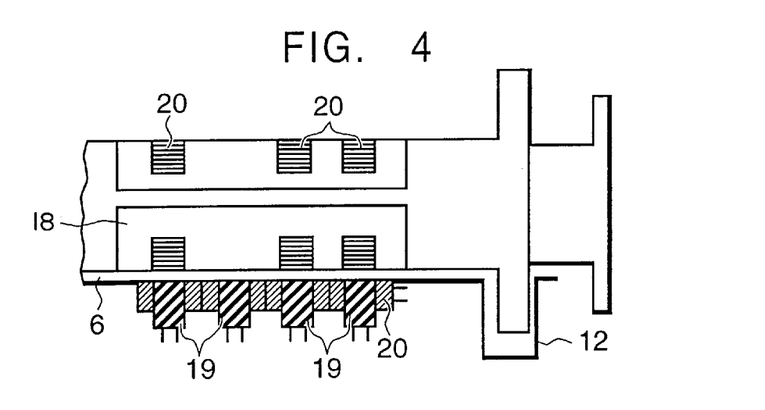
FIG. 4 shows: part of a syringe and a cooperative activation/receiving means.

A further system, shown in FIG. 4, for tagging the syringe is envisaged that utilises a circumferential magnetic ink bar code on a syringe label 18, and Hall effect transducers 19 mounted within the pump 6. Magnetic ink bars 20 are printed on the syringe label 18 such that when the syringe is mounted on the pump 6 the ink bars 20 lie adjacent to the transducers 19 mounted within the pump 6.

The transducers are composed of Hall effect devices mounted within electromagnets 20. The common magnetic inks, such as those found on bank cheques, behave as soft magnets and may not be relied upon to retain magnetism for long periods. To read the magnetic label described, the label is first magnetised by energizing the electromagnets 20 wound around each sensor. This produces a magnetic field to activate the magnetic ink bars 20. The current within the electromagnets 20 is reduced to zero and the magnetic flux produced by the remnant magnetism within the ink bars 20 is sensed by the Hall effect devices opposite each ink bar. The presence and absence of magnetic bars 20 may be used to denote the drug type and concentration.

The sensor system does not have to utilise Hall effect transducers. Alternative technologies are becoming available such as thick film transducers that utilise magneto-resistive properties of materials.

Figure 5:
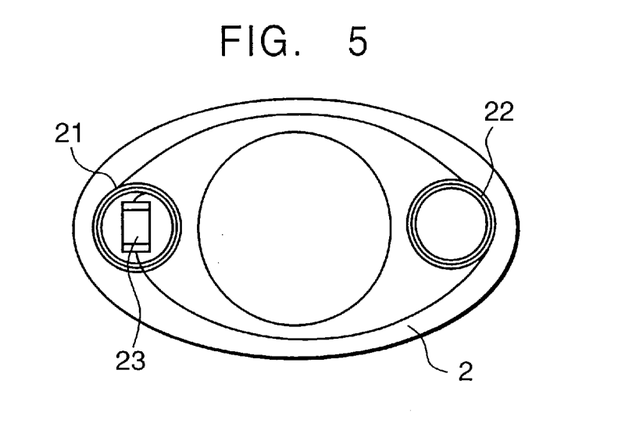
FIG. 5 shows another embodiment of syringe finger grip.

Alternatively, as a result of a search for technologies applicable to automatic syringe identification as just described, well known systems have emerged that utilise electrical or magnetic resonance. An electrically resonant circuit composed of inductance and capacitance will have a resonant frequency $$\frac{1}{2\pi\sqrt{LC}}$$

where L is the inductance of the circuit and C its capacitance. FIG. 5 shows an inductor wound as two aerial coils 21,22 in series, connected to each end of a chip capacitor 23. The inductor may be conductive ink printed on a carrier film suitable for moulding into the syringe finger grip 2, or may be insulated wire.

The activation means will scan the frequencies of interest by transmitting power from an aerial positioned near the groove 12 provided for the syringe finger grips 2b. At the resonant frequency of the circuit within the syringe, the effective impedance of the transmitter aerial will fall substantially. The fall in impedance can be detected and the frequency of resonance measured. The control system of the pump may thus identify the drug type and concentration by the resonant frequency of the syringe's circuit.

Alternatively, as the result of a search for technologies applicable to automatic syringe identification as just described, magnetostrictive systems such as those disclosed in U.S. Pat. No. 4,510,490 and WO 92/12402 emerged as another possibility. The system incorporates a tag 2c moulded into the syringe finger grip projection 2b, and a detector (which both activates and receives) in the body of the syringe pump 6.

The tag is composed of a thin strip of "electrical" steel ribbon overlying a thin steel strip of hard magnetic steel of similar dimension. In the form envisaged, the strips are approximately 10 mm long and 2.5 mm wide. The combined thickness of the two strips is about 0.5 mm.

A tag constructed in the way described will resonate at radio frequencies when subjected to an incident magnetic (not electric) field at its resonant frequency, eg 100 KHz. The resonant frequency is primarily determined by the dimensions and composition of the electrical steel strip and the strength of its associated bias magnet. Thus by varying the length of the electrical alloy strip or the strength of the bias magnet, the resonant frequency may be preset according to the contents of the syringe.

Electric power transformers are designed such that electrical energy in one winding is transferred to a second winding via a conversion to and from an "isolating" magnetic field constrained within a steel core. The efficiency of the transformer has a high dependence on the energy lost to the core during the conversion of the electrical energy into and out of the magnetic field. This energy is absorbed in eddy currents within the steel and elastic stains caused by the expansion and contraction of the magnetic domains within the atomic structure of the steel.

These strains act through the magnetostrictive effect, which is analogous to but smaller than the better known piezoelectric effect. To reduce the effects of eddy currents, the electrical resistance of the steel is increased with the addition of silicon. Thus transformer core steel is very efficient at conducting magnetism, enabling the low energy, magnetostrictive properties to be exploited in other applications.

The electric power transformer industry has dedicated much resource to improvements in the conversion efficiency of its products. In particular, improvement has been gained through the use of better materials in the transformer core. Eddy current losses have been reduced by increasing the resistance of the steel without reducing magnetic permittivity. Some of these high resistance, high permittivity steels exhibit significant magnetostriction making them suitable for use as resonators in the current application.

Figure 6:
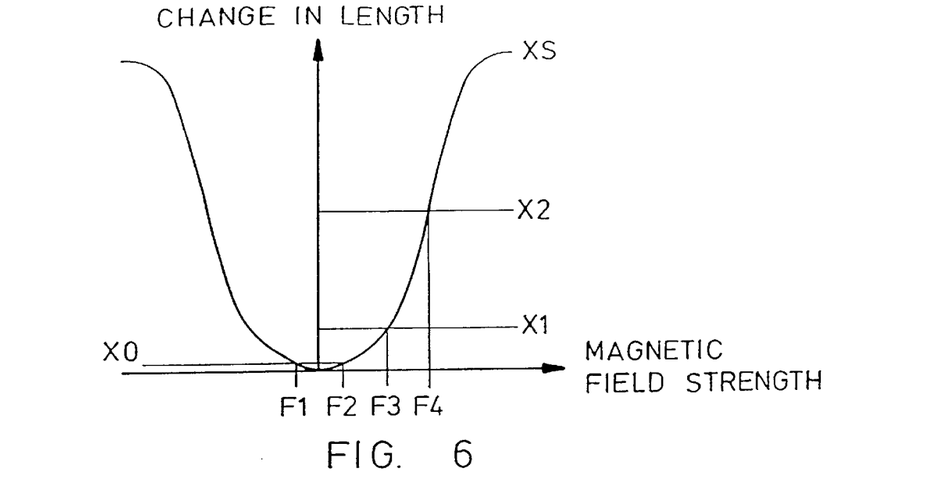
FIG. 6 shows the principle of the magnetostrictive effect employed in some embodiments of the present invention.

Referring to FIG. 6, the magnetostrictive effect is shown by an increase in the length of a steel ribbon when in the presence of a magnetic field. As the field strength is increased, so the ribbon's length increases to the point of saturation (XS). Thus under the influence of a field strength F3 the ribbon has extended by X1. Increasing the strength of the field to F4 further increases the length by X2.

The U shape of the curve indicates that when the field is reduced from F1 to zero, reversed and increased to F2, the ribbon will contract to a minimum length at a field strength of zero and extend again by X0 at a field strengt h of F2. Thus if the magnetostrictive property of the ribbon is to be exploited it should be held in a bias fmield of F4 such that it is on the steepest part of the curve. Under the influence of this bias field, the material's length will exhibit the greatest sensitivity to any changes in the incident magnetic field strength.

Two systems have been identified in particular which exploit the use of biased magnetostrictive materials and which can be exploited as potential data carrier devices in the form of identification markers for the syringe. The first uses the fundamental resonant frequency of the magnetostrictive material steel strip and the second employs harmonics of that resonant frequency. Both systems use a steel strip of magnetostrictive material developed for the power transformer industry, biased with a strip of permanent magnet of similar dimensions. The two strips are sealed and held in a cavity within the sy ringe finger grip projection 2b, such that the magnetostrictive element can freely vibrate but is constrained to be in close proximity to or touching the bias magnet.

Figure 7:
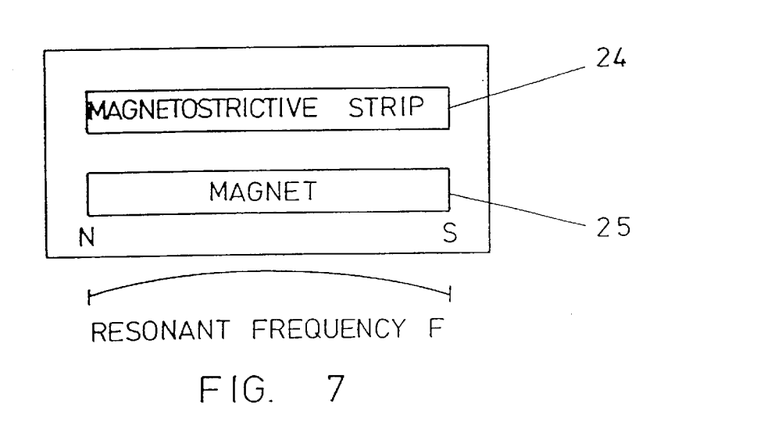
FIG. 7 explains the principle of a first magnetostrictive data carrier which may be used in embodiments of the present invention.

Fundamental Resonance System (FIG. 7)

The identification device consists of the two steel strips a s described above. The s teel alloy strip 24 is a magnetostrictive material biased to its sensitive region by the associated magnet 25. When the tag is subject to an incident, additional magnetic field, its length will change.

If the incident magnetic field produced by the activation means within the syringe pump is varying in intensity, the tag will expand and contract in sympathy with the field. As the incident field frequency is increased in a scan of different frequencies, a frequency will be reached at which the tag mechanically resonates, expanding and contracting at an amplitude greater than would be attributable to the peak values of the incident field alone. This frequency is primarily determined by the dimensions of the magnetostrictive strip and its ductility. The resonance may be detected by the receiving means in the syringe pump as described later.

FIG. 7 shows the standing wave that has formed in the magnetostrictive material at the resonant frequency F. At resonance there are null points (no deviation from the mean position) at the ends of the strip. Even harmonic frequency waves may also be excited which have nulls at the ends of the strip, although they will be of a smaller amplitude and easily discriminated from the fundamental frequency.

Figure 8:
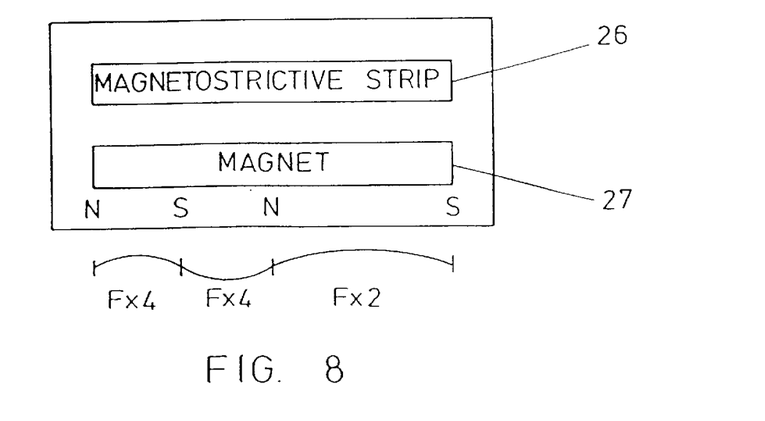
FIG. 8 shows the principle of a second magnetostrictive data carrier which may be used in alternative embodiments of the present invention.

Harmonic Resonance System (FIG. 8)

FIG. 8 shows how the standing wave would form in a magnetostrictive strip 26 biased with two magnets 27. The first is a ¼ of the length of the strip and the second ½ the length. In the proposed system the pairs of poles are "printed" on the same magnetic strip 27 in a similar manner to the way music is recorded on magnetic tape by cassette recorders. The manner in which this is achieved will be readily apparent to the man skilled in the art. The strip 26 will have the same fundamental resonance as the strip 24 in FIG. 7. However, in addition two strong harmonics may be excited at twice and four times the fundamental frequency. The two magnets 27 could of course alternatively be separate magnetic strips.

Similar to the fundamental resonance tag, this tag will resonate at its fundamental frequency as determined by its shape and ductility. However, in addition it may be programmed to resonate at chosen harmonic frequencies enabling information to be represented by the presence of absence of the different harmonics. More harmonics than those shown could be employed.

A fundamental resonance system as described has already been proposed for example in U.S. Pat. No. 4,510,490, while a harmonic resonance system has already been proposed also, for example in WO 92/12402. These previously proposed resonance systems could be employed in embodiments of the present invention.

Figure 9:
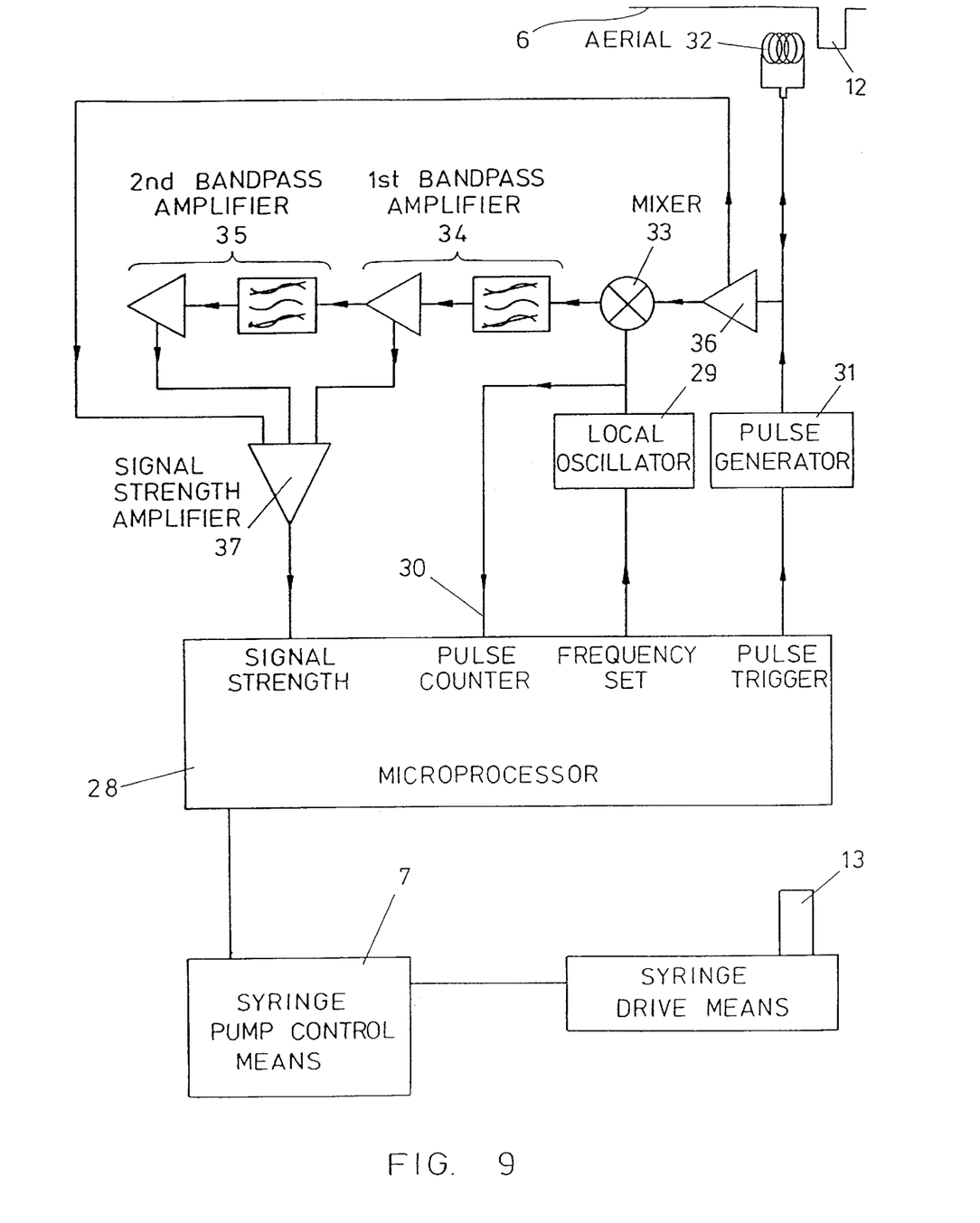
FIG. 9 shows an activating and receiving means for a syringe pump which is cooperable with magnetostrictive data carriers.

Resonance Detection System (FIG. 9)

FIG. 9 shows a circuit designed to act as the activation means and the receiving means within the body of the syringe pump 6. It will detect the resonant frequencies of the two magnetostrictive tag systems described above, and employs the heterodyne principle of received signal processing.

A micropro cessor 28 of the activation/receiving means is shown coupled to the syringe pump control means 7, which is in turn shown coupled to the syringe drive means comprising the piston 13.

To eliminate set up costs during manufacture the microprocessor 28 calibrates the local oscillator frequencies of oscillator 29 at the "pulse counter" input 30, against its own quartz crystal clock each time the system is powered up. Following this self calibration, the microprocessor 28 will have access tio a table of all the resonant frequencies of interest and the "frequency set" voltages required for the local oscillator to detect them.

Detection of a resonant frequency is initiated by the microprocessor 28 setting the appropriate local oscillator frequency and triggering a pulse from the pulse generator 31. The pulse will have a duration of half the period of the resonant frequency of interest. The current resulting from the pulse will cause a magnetic field to be formed around the aerial coil 32, which is mounted within the syringe pump 6 in close proximity to the tag 2c when the syringe is mounted on the syringe pump 6.

In response to the magnetic pulse, the magnetostrictive element of the tag will distort and relax. However, if the pulse duration is ½ the wavelength of a resonant frequency, the tag will continue to resonate after the pulse. The vibration of the magnetostrictive element within the magnetic field of its bias magnet will cause a very weak, oscillating magnetic field to be emitted from the tag.

This weak field will generate a current in the aerial 32 which is amplified and fed to the mixer stage 33 of the detector. The mixer 33 will produce the difference frequency of the received signal and the local oscillator 29. The difference frequency is fed to a two stage, very narrow, bandpass amplifier 34, 35. Thus by choosing the appropriate local oscillator frequency, the difference frequency should be the centre frequency of the bandpass amplifiers 34, 35.

Any signal received by the aerial 32 of the correct frequency will receive significant amplification by amplifier 36. A signal is taken from each of the three amplifiers 34, 35, 36 to the signal strength amplifier 37. The resultant signal strength is fed back to the microprocessor 28.

By comparing the signal strength before the pulse (but after the local oscillator frequency has been set) with that immediately following the pulse, the microprocessor 28 can be programmed to determine whether a resonance was present. The process is repeated for each frequency of interest.

The activating and receiving system described above is not the simplest implementation possible. Simpler systems could be developed which utilise separate transmit and receive coils enabling continuous transmission of the exciting field. This method is used in shop door security systems. However, it is preferable that it should be possible to fit the same design of activating and receiving circuitry into a number of different manufacturers' syringe pumps. In this respect the single coil system places less mechanical constraints on the syringe pump than does a double coil system, and is therefore preferable.

Each detected resonance or harmonic may provide one item of information. Thus, for example, detection of two different fundamental resonances from two strip devices according to FIG. 7 could provide an identification of a particular medicament and its concentration, as could the detection of say a fundamental resonance and a harmonic, or two harmonics, from a single strip according to FIG. 8.

There have been disclosed embodiments of the invention wherein a syringe is provided with one or more data carrier devices to carry data relating to a medicament contained or to be contained in the syringe. Preferably, the syringe has two data carrier devices mounted on opposite sides of the syringe so that at least one of the devices will always be able to cooperate with an activation/receiving means provided within the syringe pump.

Preferably two data carrying devices are provided in the respective opposite finger grip projections of a syringe finger grip.

However, embodiments such as those shown in FIGS. 3 and 5 need only have one data carrying device (transponder 15 or chip capacitor 23) and the use of two aerial coils on the two finger grip projections makes this possible.

For safety, the or each data carrier device should not be insertable into a syringe by the user, and moreover should not be reusable to reactivate the syringe pump aieter the syringe has been emptied.

To assist in achieving this, the or each data carrier device and any connections should be embedded within their surrounding material, preferably by moulding or encapsulation.

Also, the or each data carrying device could be adapted to be incapacitated after one use. In the case of the transponder, it or the pump could be programmed to achieve this. The magnetostrictive tags could have their bias magnets demagnetised by generating a suitable field around the detector aerial. The ability to demagnetise the bias magnet will require a specific choice of material for the bias magnet if erasure is not to occur during transport or storage and yet is not to require impractical demagnetising field strengths. The man skilled in the art will be able to make this choice of bias magnet material in dependence upon the particular requirements of any particular embodiment.

It has however been found that a particularly suitable material for the magnetostrictive strip is Metglas (trade mark) 2605 in most embodiments.

These measures are intended to limit the potential for misuse of either a pre-filled syringe or a cooperable syringe pump. For example, the pre-filled syringe should not be reused with an alternative medicament, or even re-used with a re-filling of the original medicament.

Moreover the computer controlled syringe pump should not be used with an alternative medicament and/or an inappropriate mathematical model incorporated in its programming.

Although a plurality of data carrier means activatable by suitable fields have been specifically disclosed herein, it is to be understood that the present invention is not restricted to these. Any electrically and/or magnetically operable device suitable for the indicated purpose may be employed in embodiments of the present invention. In particular, it is to be understood that the operation of the data carrier means need not be wholly electrical and/or magnetic, and thus for example optical and/or acoustic elements may be employed in conjunction with electrical and/or magnetic devices in alternative embodiments.

It is further to be understood that the invention is not restricted to magnetic and/or electrical fields to be put into practice. Any other type of field (electromagnetic or otherwise) which is suitable to activate a cooperable data carrier means in accordance with the present invention can be employed. Thus, in alternative embodiments of the invention for example fields comprising radiation anywhere within the electromagnetic spectrum may be employed, and also other fields such as acoustic or other non-electromagnetic fields may be employed in suitably adapted embodiments.

Further, although a preferred location for the data carrier means has been disclosed to be in the finger grip for a syringe, it is to be understood that in a syringe specifically intended for use with a syringe pump, projections 2b in FIG. 1 may no longer be intended actually to be used as finger grips. Nevertheless, this has been a convenient manner in which to describe projections 2b in the present document, and it is to be understood as being non-limiting.

It is also to be understood that the data carrier means could be located elsewhere in or on the syringe for example on a label as shown in FIG. 4, or embedded or molded within the syringe barrel 1, or on or in some other specially-provided additional part or projection not specifically disclosed herein.

I claim:

1. A syringe pump cooperable with a syringe having data carrier means to carry data relating to a medicament associated with the syringe, comprising:
   activation means to emit an activating signal adapted to cause syringe data carrier means operable in at least one of an electrical mode and a magnetic mode to emit data in response to activation by said activating signal;
   receiving means for receiving data emitted in response to activation by said activating signal;
   drive means for operating a syringe to deliver to a patient medicament contained in a syringe operated by said drive means; and
   control means coupled to said receiving means and to said drive means to operate the drive means taking into account data received by the receiving means.

2. A syringe pump according to claim 1, comprising a mounting region to receive a syringe to be operated by the syringe pump, wherein said activation means and said receiving means are located adjacent to said mounting region.

3. A syringe pump according to claim 2, wherein said mounting region comprises a recess to receive a projection, of a syringe received by said mounting region, on which a data carrier means is mounted.

4. A syringe pump according to claim 3, wherein said activation means and said receiving means are located adjacent to said recess.

5. A syringe pump according to claim 1, wherein the activation means is operable to produce a magnetic pulse which will cause a suitable magnetically resonant data carrier means on a syringe to resonate, and said receiving means to operate to detect such resonance.

6. A syringe pump according to claim 1, wherein said control means is adapted such that any one syringe can be operated by said drive means only once.

7. A method for automatically identifying at least one of a medicament and a property of a medicament, comprising providing with a syringe which is associated with said medicament, data carrier means comprising a device which is operable in at least one of an electrical mode and a magnetic mode to emit data and identifying said at least one of said medicament and said property thereof, in response to activation by an activation signal applied by an external means.

8. A partially disassembled syringe comprising a barrel, a plunger and a finger grip in an assembled state with the plunger fitting closely within the barrel and the finger grip being inserted in an open end of the barrel, there being a plunger rod provided separately and disassembled from the plunger, and the syringe being provided with data carrier means to carry data relating to a medicament associated with the syringe, wherein the data carrier means comprises a device which is operable in at least one of an electrical mode and a magnetic mode to emit data in response to activation by an activating signal applied by an external means.

9. An instrument for administering a medicament to a patient comprising:
   a syringe having data carrier means to carry data relating to a medicament associated with said syringe, wherein said data carrier means comprises a device which is operable in at least one of an electrical mode and a magnetic mode to emit data in response to activation by an activating signal applied by an external means; and
   a syringe pump cooperable with said syringe and comprising:
   activation means to emit said activating signal to cause said data carrier means to emit data;
   receiving means for receiving the data emitted from said data carrier means;
   drive means for operating said syringe to deliver to a patient medicament contained in said syringe; and
   control means coupled to said receiving means and to said drive means to operate said drive means taking into account data received from said data carrier means by said receiving means.

* * * * *

UNITED STATES PATENT AND TRADEMARK OFFICE
CERTIFICATE OF CORRECTION

PATENT NO.   : 6,019,745
DATED        : February 1, 2000
INVENTOR(S)  : Gray

It is certified that error appears in the above-identified patent and that said Letters Patent is hereby corrected as shown below:

<u>Title page,</u>
Please add: -- [30] Foreign Application Priority Data,
May 4, 1993    [GB]   United Kingdom      9309150.0
Apr. 28, 1994  United Kingdom     PCT/GB94/00909 --

Signed and Sealed this

Second Day of April, 2002

Attest:

JAMES E. ROGAN
Attesting Officer     Director of the United States Patent and Trademark Office